United States Patent
Chen et al.

(10) Patent No.: US 8,813,744 B2
(45) Date of Patent: Aug. 26, 2014

(54) ANESTHETIC VAPORIZER AND TEMPERATURE COMPENSATION UNIT

(75) Inventors: Donghua Chen, Shenzhen (CN); Daoming Gong, Shenzhen (CN); Zhiwei Qiao, Shenzhen (CN)

(73) Assignee: Shenzhen Mindray Bio-Medical Electronics Co., Ltd, Shenzhen (CN)

( * ) Notice: Subject to any disclaimer, the term of this patent is extended or adjusted under 35 U.S.C. 154(b) by 897 days.

(21) Appl. No.: 12/687,632

(22) Filed: Jan. 14, 2010

(65) Prior Publication Data

US 2010/0180893 A1 Jul. 22, 2010

(30) Foreign Application Priority Data

Jan. 16, 2009 (CN) .......................... 2009 1 0105094

(51) Int. Cl.
*F23D 11/00* (2006.01)
*A61M 16/18* (2006.01)

(52) U.S. Cl.
CPC ....... *A61M 16/18* (2013.01); *A61M 2205/3372* (2013.01)
USPC .................. 128/203.26; 128/203.14; 261/39.1

(58) Field of Classification Search
USPC ........... 128/203.14, 203.26; 261/39.1; 263/53
See application file for complete search history.

(56) References Cited

U.S. PATENT DOCUMENTS

| | | | | |
|---|---|---|---|---|
| 2,553,446 A | * | 5/1951 | Edmondson et al. ..... | 128/203.14 |
| 3,534,732 A | * | 10/1970 | Bickford .................... | 128/203.14 |
| 3,575,168 A | * | 4/1971 | Jones et al. .............. | 128/203.14 |
| 3,588,057 A | | 6/1971 | Lubeck | |
| 3,630,438 A | * | 12/1971 | Bickford ......................... | 236/53 |
| 3,651,805 A | * | 3/1972 | Breiling .................... | 128/203.25 |
| 3,671,024 A | * | 6/1972 | Breiling ........................ | 261/39.1 |
| 4,017,566 A | * | 4/1977 | Seidel .............................. | 261/56 |

(Continued)

FOREIGN PATENT DOCUMENTS

| | | |
|---|---|---|
| CN | 1038938 A | 1/1990 |
| CN | 1132100 A | 10/1996 |
| CN | 200987822 Y | 12/2007 |
| GB | 2 355 666 A | 2/2001 |

OTHER PUBLICATIONS

Chinese Search Report dated Aug. 12, 2009 for China patent application No. 200910105094.8.
English translation of abstracts for CN1038938.

(Continued)

*Primary Examiner* — Scott Medway
(74) *Attorney, Agent, or Firm* — Kory D. Christensen; Stoel Rives LLP

(57) ABSTRACT

An anesthetic vaporizer and a temperature compensation unit are disclosed. The temperature compensation unit, which cooperates with a vaporizing chamber having a bottom wall, includes a first device connected to the bottom wall of the vaporizing chamber for contacting with liquid anesthetic agent in the vaporizing chamber and changing in length according to temperature change of the liquid anesthetic agent, and a second device connected to the vaporizing chamber. A gas flow gap through which a gas flow passes is formed between the first and second devices. The gas flow gap becomes larger as temperature of the liquid anesthetic agent rises and smaller as the temperature of the liquid anesthetic agent drops. Since the first device is connected with the bottom wall of the vaporizing chamber, the first device will directly contact with the liquid anesthetic agent regardless of the liquid level of the anesthetic agent, as long as there is liquid agent in the vaporizing chamber; therefore the efficiency of heat exchange is high and the effect of temperature compensation is good.

20 Claims, 4 Drawing Sheets

(56) References Cited

U.S. PATENT DOCUMENTS

| | | | |
|---|---|---|---|
| 4,444,182 A | * | 4/1984 | Gregory .................. 128/204.14 |
| 4,693,853 A | * | 9/1987 | Falb et al. .................. 261/39.1 |
| 4,770,168 A | * | 9/1988 | Rusz et al. ............... 128/203.12 |
| 4,879,997 A | | 11/1989 | Bickford |
| 4,919,125 A | | 4/1990 | Heaton et al. |
| 5,146,915 A | * | 9/1992 | Montgomery ........... 128/203.14 |

| | | | |
|---|---|---|---|
| 2003/0079746 A1 | * | 5/2003 | Hickle .................... 128/203.12 |
| 2005/0133030 A1 | | 6/2005 | Fiedorowicz |

OTHER PUBLICATIONS

English translation of abstracts for CN200987822.
English translation of abstracts for CN1132100.

* cited by examiner

ANESTHETIC VAPORIZER AND TEMPERATURE COMPENSATION UNIT

CROSS-REFERENCE TO RELATED APPLICATIONS

The present application claims priority to Chinese Patent Application No. 200910105094.8, filed on Jan. 16, 2009, which is hereby incorporated by reference in its entirety.

FIELD OF THE INVENTION

The present disclosure relates to an anesthetic vaporizer and a temperature compensation unit.

BACKGROUND OF THE INVENTION

An anesthetic vaporizer is an apparatus that can be used to effectively vaporize a liquid anesthetic agent, and can precisely input the liquid anesthetic agent at a certain concentration into an anesthesia breathing circuit. The anesthetic vaporizer typically comprises a fresh gas inlet, a pressure compensation unit, a fresh gas cut-off valve, a wick unit, a bypass circuit, a temperature compensation unit, a concentration control unit, a mixed gas outlet, a filling unit, and a vaporizing chamber. The vaporizing chamber is a reservoir for storing liquid anesthetic agent. The wick unit is provided within the vaporizing chamber. A part of the wick unit is immersed into the anesthetic agent such that the wick unit is filled with saturated anesthetic vapor.

After fresh gas flows into the vaporizer through the fresh gas inlet, a part of the gas flows into the wick unit via the fresh gas cut-off valve after passing through the pressure compensation unit. When the fresh gas flows through the wick unit, the fresh gas will be mixed with parts of the anesthetic vapor. The fresh gas carrying the anesthetic vapor flows into the concentration control unit after passing through the wick unit. The other part of the fresh gas flows into the bypass circuit, then flows into the concentration control unit after passing through the temperature compensation unit, and meets the fresh gas carrying the anesthetic vapor in the concentration control unit. By controlling the concentration control unit, the two streams of gases are mixed at a certain ratio of anesthetic gas and outputted out of the vaporizer from the mixed gas outlet.

When the vaporizer is used continuously, the temperature of the vaporizer drops since the anesthetic agent has to absorb heat to vaporize, which in turn reduces the evaporation speed of the anesthetic agent since the evaporation speed of the liquid decreases as the temperature drops. Thus, the concentration of the anesthetic vapor outputted from the vaporizer is reduced accordingly. As the temperature within the vaporizing chamber rises, the pressure of the saturated vapor increases, and then the concentration of the outputted anesthetic vapor will gradually increase.

In order to solve the problem of the change of the output concentration of the anesthetic vapor due to the change of temperature, the flow is typically adjusted by a temperature compensation unit with flow adjustment mechanism. As the temperature within the vaporizing chamber changes, the temperature compensation unit will change the nominal diameter of a valve port thereof to increase or decrease the flow of the dilute gas stream passing through the bypass circuit, such that the concentration output of the vaporizer does not change due to the change of temperature.

A conventional temperature compensation unit, as shown in FIG. 1 comprises an upper valve port assembly and a lower valve port assembly. The upper valve port assembly comprises an upper valve port 46 and a plurality of metal rods 45 having a low temperature linear expansion coefficient. The metal rods 45 are assembled with a copper body 44 having a high temperature linear expansion coefficient. The lower valve port assembly, which is generally in the form of "T", comprises a lower valve port 47, an upstanding rod 49 and a fixing nut 50. The upstanding pod 49 has the low temperature linear expansion coefficient. The upstanding pod 49 is assembled with a copper valve seat 48 having a high temperature linear expansion coefficient so as to define two temperature sensitive valves. The fresh gas flowing in through the fresh gas inlet 41 enters between the upper and lower valve ports via the bypass circuit 45, and the mixed gas is outputted via the mixed gas outlet 51. When the temperature within the vaporizing chamber changes, both the upper and lower valve ports move relative to their initial positions, so as to change the caliber between the two valve ports, thereby achieving the purpose of temperature compensation.

However, this type of compensation unit has disadvantages, such as the following: (1) the lower valve port assembly, which has a relatively short length, is only immersed into the upper space in the vaporizing chamber while remaining a certain distance away from the bottom of the vaporizing chamber. During the anesthetic operation, when the liquid level of the anesthetic is below the bottom of the lower valve port assembly, the agent will no longer directly contact the metal valve seat of high temperature linear expansion coefficient, which is disadvantageous to heat exchange and reduces the compensation effect. (2) Since the upper valve port assembly is installed with a plurality of metal rods which are required to be adjusted when the vaporizer is calibrated, the structure is complicated, and the requirements for installation and adjustment are accordingly relatively high, causing excessive difficulties and expense for installation and adjustment of the compensation unit.

SUMMARY OF THE INVENTION

The technical problem to be solved by some embodiments of the present invention is to provide an anesthetic vaporizer and a temperature compensation unit which can improve the temperature compensation effect.

The technical solution adopted by some embodiments of the present invention to solve the above technical problem is directed to a temperature compensation unit for an anesthetic vaporizer, which cooperates with a vaporizing chamber having a bottom wall, including a first device connected with the bottom wall of the vaporizing chamber for contacting with a liquid anesthetic agent in the vaporizing chamber and changing in length according to temperature change of the liquid anesthetic agent in the vaporizing chamber, and a second device connected with the vaporizing chamber, with a gas flow gap through which a gas flow passes being formed between the first and the second devices, wherein the gas flow gap becomes larger as the temperature of the liquid anesthetic agent rises and smaller as the temperature of the liquid anesthetic agent drops.

An anesthetic vaporizer may include an fresh gas inlet, a mixed gas outlet, a main gas path block having a gas flow passage, and a vaporizing chamber having a bottom wall. The fresh gas inlet is communicated with the gas flow passage via a first gas branch circuit and a second gas branch circuit. The gas flow passage is communicated with the mixed gas outlet. The first gas branch circuit may include a bypass circuit and a temperature compensation unit arranged in sequence. The second gas branch circuit may include a wick unit which is provided within the vaporizing chamber. The temperature compensation unit may include a first device connected with the bottom wall of the vaporizing chamber for contacting with a liquid anesthetic agent in the vaporizing chamber and changing in length according to temperature change of the liquid anesthetic agent in the vaporizing chamber, and a second device connected with the vaporizing chamber via the main gas path block, with a gas flow gap with which the gas flow passage is communicated being formed between the first and second devices, wherein the gas flow gap becomes larger as the temperature of the liquid anesthetic agent rises and smaller as the temperature of the liquid anesthetic agent drops.

DETAILED DESCRIPTION OF THE INVENTION

Figure 1:
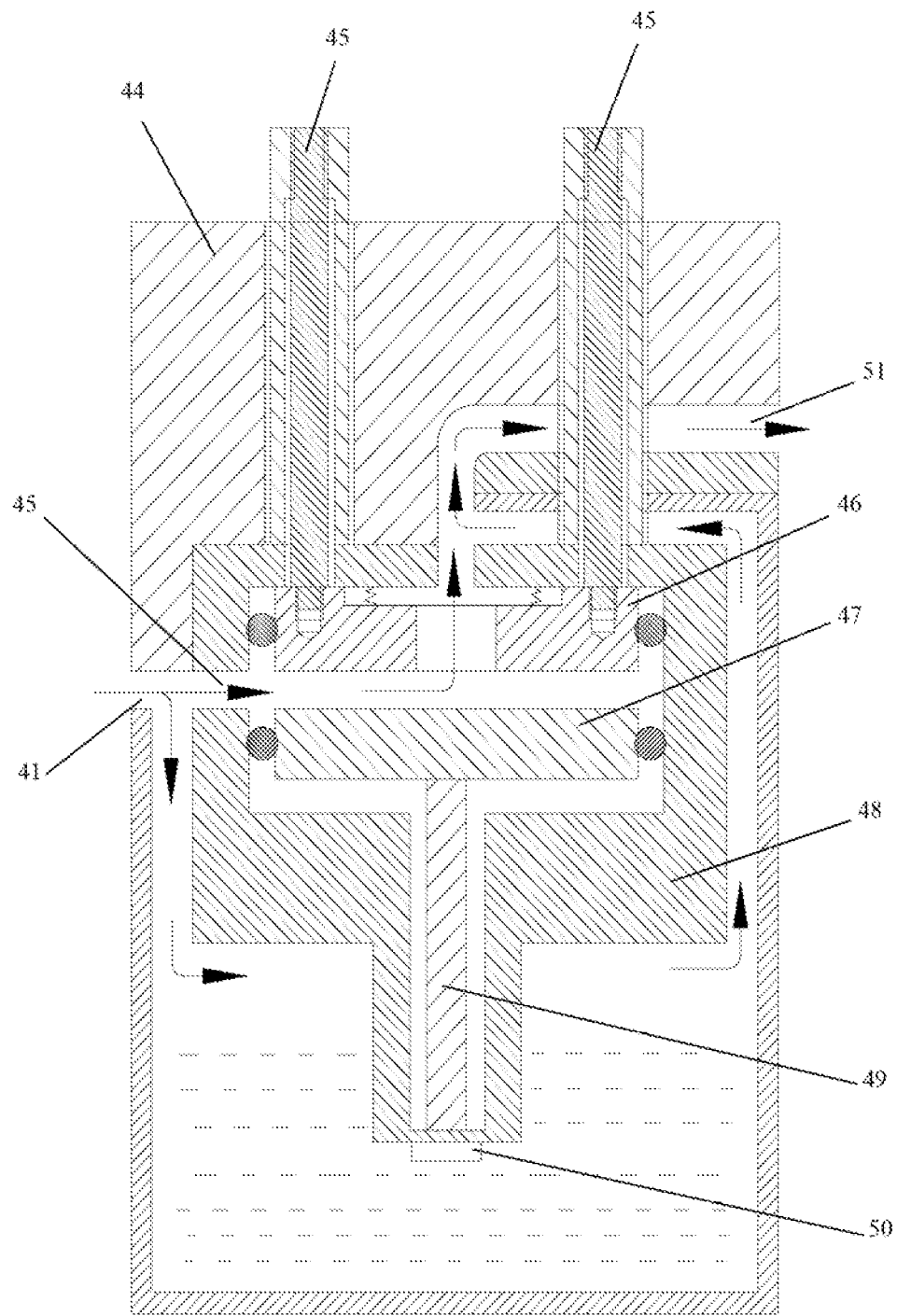
FIG. 1 is a structural schematic view of a conventional temperature compensation unit.
Figure 2:
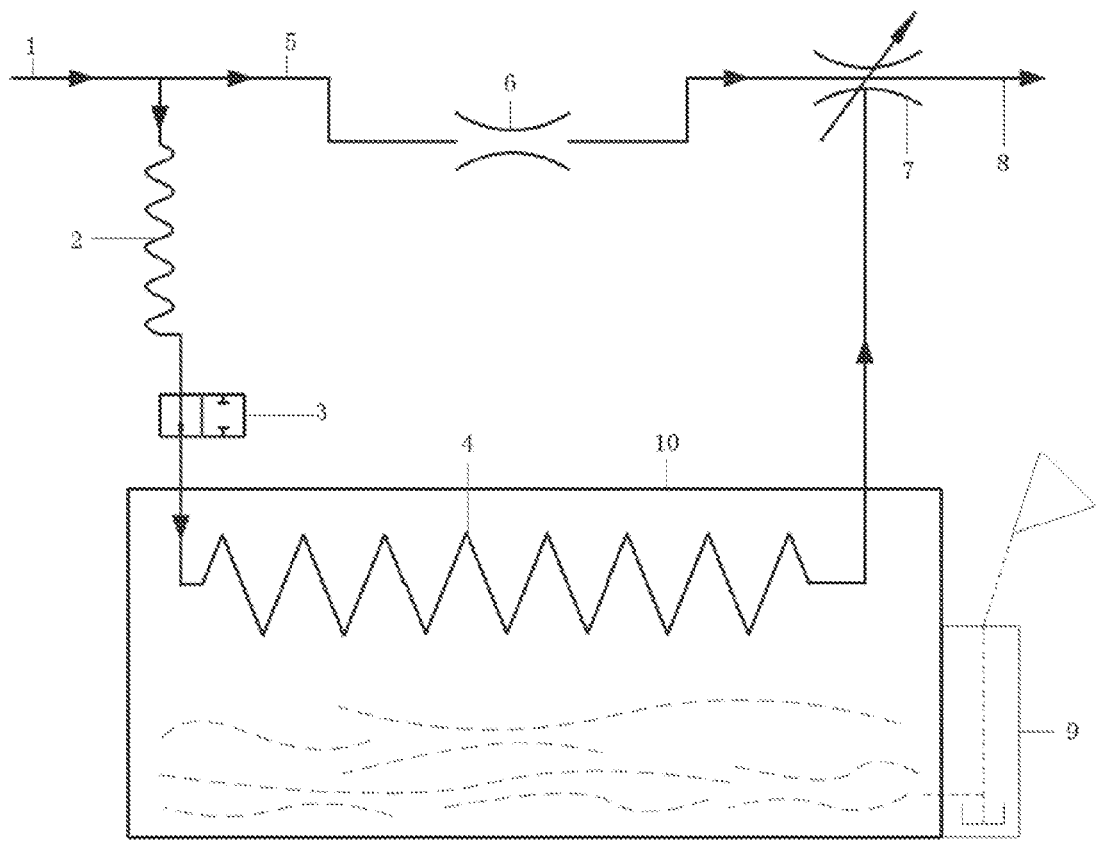
FIG. 2 is a principle schematic view of gas path of an anesthetic vaporizer according to an embodiment of the present disclosure.
Figure 3:
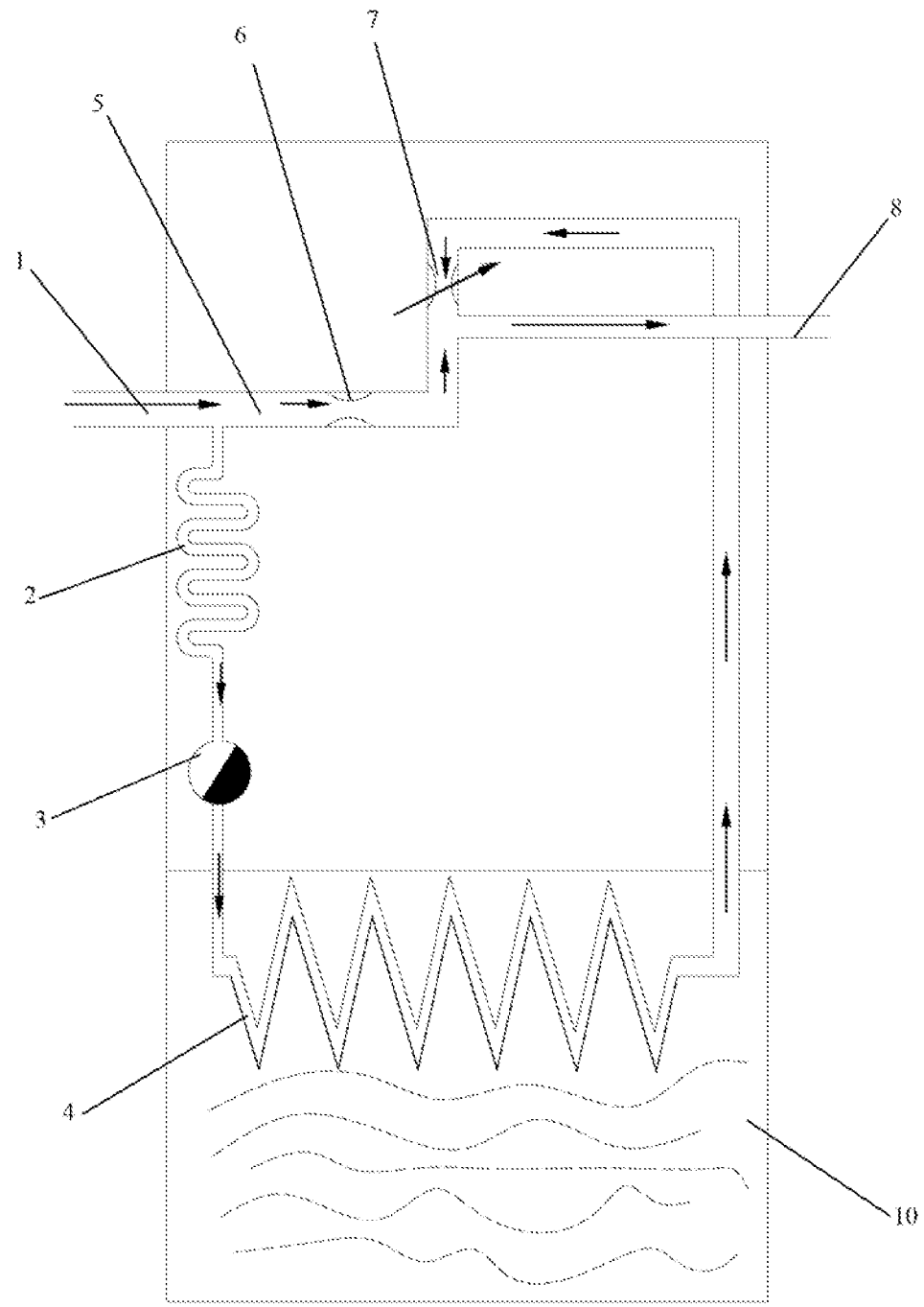
FIG. 3 is a structural schematic view of an anesthetic vaporizer according to an embodiment of the present disclosure.
Figure 4:
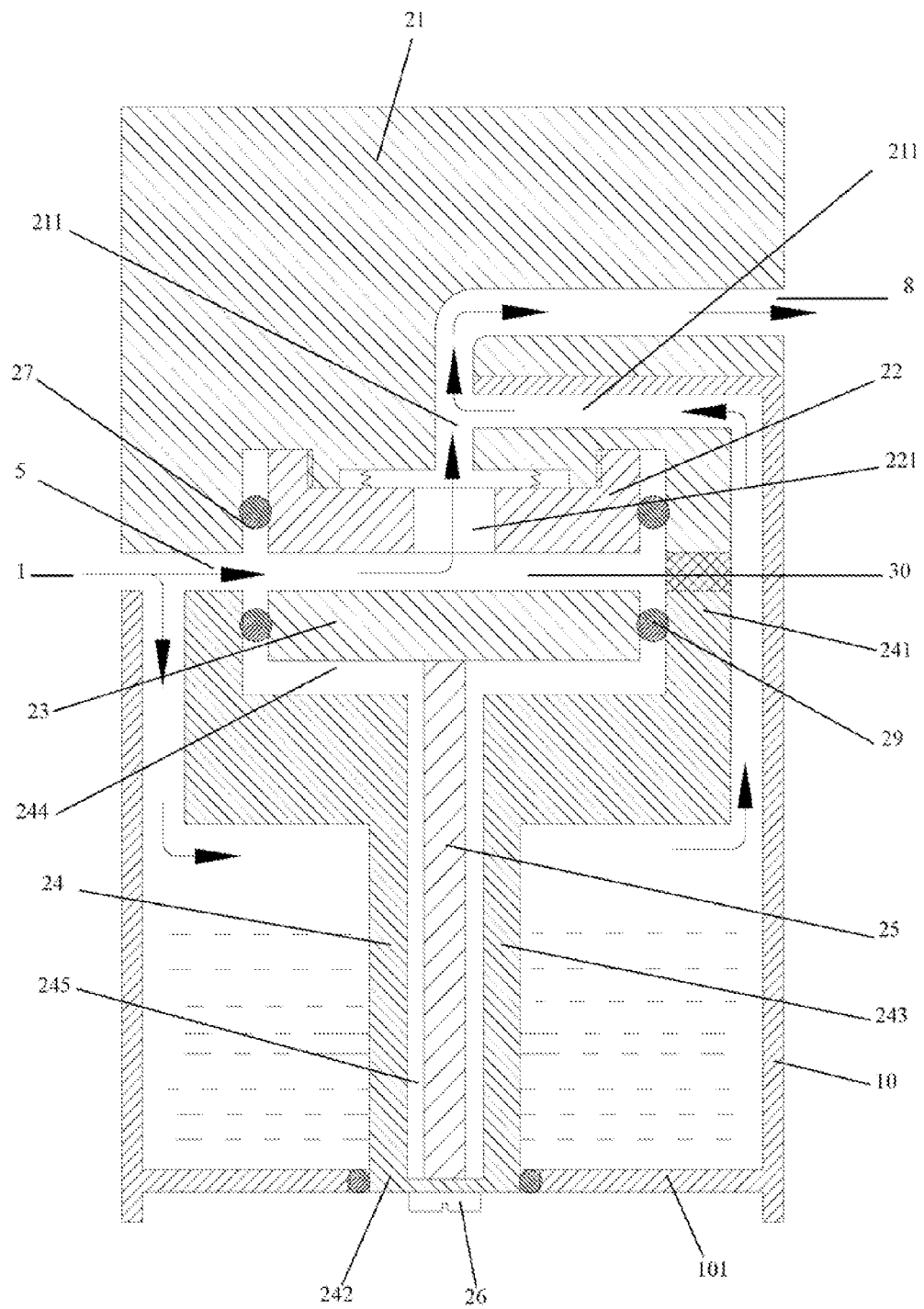
FIG. 4 is a structural schematic view of a temperature compensation unit according to an embodiment of the present disclosure.

As shown in FIGS. 2-4, an anesthetic vaporizer according to an embodiment of the present disclosure may include a fresh gas inlet 1, a pressure compensation unit 2, a fresh gas cut-off valve 3, a wick unit 4, a bypass circuit 5, a temperature compensation unit 6, a concentration control unit 7, a mixed gas outlet 8, a filling unit 9, a vaporizing chamber 10 and a main gas path block 21. The pressure compensation unit 2 which serves to compensate for pressure can prevent gas from flowing reversely when the pressure at the mixed gas outlet 8 changes and stabilize the gas flow speed when the pressure at the fresh gas inlet 1 changes. The vaporizing chamber 10 may be implemented as a reservoir having a bottom wall 101 for storing liquid anesthetic agent. The wick unit 4, which may be positioned within the vaporizing chamber 10, may have a part thereof being immersed into the liquid anesthetic agent such that the liquid anesthetic agent can spread over the wick unit 4. The wick unit 4 may facilitate vaporization of the liquid anesthetic agent in the vaporizing chamber into gaseous state from liquid state. The greater the surface area, the better the evaporation efficiency. The filling unit 9 may serve to replenish the vaporizing chamber 10 with liquid anesthetic agent The main gas path block 21, which may be provided above the 20 vaporizing chamber 10, may have a gas flow passage 211. The concentration control unit 7 may be positioned in the gas flow passage 211 of the main gas path block 21.

The temperature compensation unit 6 may include an upper valve plate 22, a lower valve plate assembly, a valve seat 24 and an elastic sealing ring. The upper valve plate 22 may be screw coupled with the main gas path block 21. The upper valve plate 22 is formed at its center with a through hole 221 which is communicated with the concentration control unit 7 disposed in the gas flow passage 211. The outer peripheral wall of the upper valve plate 22 and the main gas path block 21 may be sealed with respect to each other by an O-shaped elastic second sealing ring 27. The lower valve plate assembly, which may be generally of T-shape, may include a lower valve plate 23 and a valve rod 25 which are arranged coaxially. The lower valve plate 23 has a diameter greater than that of the valve rod 25. The lower valve plate 23 is screw coupled with the top of the valve rod 25. The valve seat 24, which may be implemented as a metal body, contacts directly with the liquid anesthetic agent in the vaporizing chamber 10 and can have its length changed according to the temperature change of the liquid anesthetic agent. The valve seat 24 may have a top portion 241 and a bottom portion 242. An installation groove in form of step is formed in the direction from the top portion 241 to the bottom portion 242. The installation groove may include a first installation groove 244 with a relatively large inner diameter and a second installation groove 245 with a relatively small inner diameter which are arranged coaxially. The inner diameter of the first installation groove 244 is greater than that of the lower valve plate 23, and the inner diameter of the second installation groove 245 is greater than that of the valve rod 25. The upper valve plate 22 is disposed above the lower valve 23, and a gas flow gap 30 is formed therebetween. The gas flow gap 30 is communicated with the through hole 221 of the upper valve plate 22.

The top portion 241 of the valve seat is fixed, and the bottom portion 242 is hermetically fitted with the bottom wall 101 of the vaporizing chamber. The lower valve plate assembly is disposed within the installation groove of the valve seat 24 with an O-shaped elastic first sealing ring 29 being provided between the lower valve plate 23 and the groove wall of the first installation groove 244. The valve rod 25 extends downwards into the second installation groove 245. After passing downwards through the bottom portion 242 of the valve seat, the bottom of the valve rod 25 is connected with a screw adjuster 26, such that the lower valve plate assembly is positioned at the bottom portion 242 of the valve seat. The valve seat 24 is a metal body with relatively high temperature linear expansion coefficient. The valve rod 25 is made of material with relatively low temperature linear expansion coefficient, and has its length substantially unchanged due to temperature change.

After entering the anesthetic vaporizer via the fresh gas inlet 1, the fresh gas may be divided into two streams of dilution bypass gas flow and carrier gas flow. The dilution bypass gas flow enters the gas flow passage 211 of the main gas path block 21 after passing through the bypass circuit 5, the gas flow gap 30 of the temperature compensation unit 6 and the through hole 221, and finally enters the concentration control unit 7. The carrier gas flow directly enters the vaporizing chamber 10 after flowing through the pressure compensation unit 2 and the fresh gas cut-off valve 3. After entering the vaporizing chamber 10, the carrier gas flow carries the anesthetic vapor and enters the concentration control unit 7 via the gas flow passage 211 of the main gas path block 21. With the control of the concentration control unit 7, the two streams of gases are mixed at a concentration of a certain ratio and outputted out of the anesthetic vaporizer from the mixed gas outlet 8.

When the temperature of the liquid anesthetic agent within the vaporizing chamber rises, the length of the valve seat 24 is increased. Since the top portion 241 of the valve seat is fixed, the bottom portion 242 of the valve seat generates a downward relative movement with respect to the top portion 241 of the valve seat. The valve rod 25 connected with the bottom portion 242 of the valve seat moves downwards along with the valve seat 24, causing the lower valve plate 23 to move downwards relative to the upper valve plate 22. The gas flow gap 30 between the upper and lower valve plates 23 and 22 is enlarged, and the flow of the dilution bypass gas flow is increased. Since the flow volume of the fresh gas entering the anesthetic vaporizer is constant, the flow volume of the carrier gas flow entering the vaporizing chamber 10 is accordingly reduced. By increasing the flow volume of the dilution bypass gas flow to compensate for pressure increasing of the saturated vapor due to temperature rising, the concentration of the outputted anesthetic vapor is maintained constant.

When the temperature of the liquid anesthetic agent drops, the length of the valve seat 24 is decreased. The bottom portion 242 of the valve seat moves upwards relative to the top portion 241 of the valve seat and accordingly the lower valve plate 23 in turn moves upwards. The gas flow gap 30 between the lower and upper valve plates 23 and 22 is reduced, the flow volume of the dilution bypass gas flow is decreased and accordingly the flow volume of the carrier gas flow entering the vaporizing chamber 10 is increased, and the concentration of the outputted vapor is maintained constant.

The temperature compensation unit 6 may include a first device connected to the bottom wall of the vaporizing chamber 10 for contacting with the liquid anesthetic agent in the vaporizing chamber 10 and changing in length according to the temperature change of the liquid agent, and a second device connected to the vaporizing chamber 10, with a gas flow gap 30 through which the gasflow passes being formed between the first and second devices. The gas flow gap 30 is enlarged when the temperature of the liquid anesthetic agent rises and reduced when the temperature of the liquid anesthetic agent drops. Control of the size of the gas flow gap 30 is achieved by the relative movement between the first and second devices. Since the first device is connected with the bottom wall of the vaporizing chamber 10, the first device will directly contact with the liquid anesthetic agent regardless of the liquid level of the anesthetic agent, as long as there is the liquid agent in the vaporizing chamber 10; therefore, the efficiency of heat exchange is high and the effect of temperature compensation is good.

The first device may include a valve seat 24 and an upper valve plate 22, while the second device may include a lower valve plate 23. The upper valve plate 22 is fixed stationarily while the lower valve plate 23 moves upwards and downwards with the extension and retraction of the valve seat 24 in length, such that the whole temperature compensation unit 6 is readily adjusted, which effectively reduces cost. Of course, both the upper and lower valve plates 22 and 23 may alternatively move. The size of the gas flow gap 30 is adjusted by the relative movement between the upper and lower valve plates, and in turn the flow ratio of the dilution bypass gas flow to the carrier gas flow is adjusted. The lower valve plate 23 is fixed on the top of the valve rod 25, the bottom of the valve rod 25 is connected to the bottom portion 242 of the valve seat 24. The temperature linear expansion coefficient of the valve seat 24 is greater than that of the valve rod 25 such that the lower valve plate 23 moves in upwards and downwards by the maximum distance when the valve seat 24 changes in length due to temperature change. Of course, where the condition that the lower valve plate 23 can move downwards and upwards with the valve seat 24 changing in length is met, the lower valve plate 23 is alternatively installed at other positions of the valve seat 24 by the valve rod 25. The bottom of the valve rod 25 may pass through the bottom portion of the valve seat 24 and be connected with the screw adjuster 26 such that the calibration adjustment of the initial position of the lower valve plate 23 can be achieved. The number of the valve rod 25 may be one or more, preferably one such that there is only one calibration point so as to facilitate assembling, adjustment and the calibration adjustment of the initial position of the lower valve plate 23. Alternatively the temperature compensation unit 6 may not be provided with the valve rod 25, and instead the lower valve plate 23 is directly positioned on the valve seat 24. When the valve seat 24 is changing in length due to temperature change, the lower valve plate 23 may accordingly move upwards and downwards to implement the adjustment of the gas flow gap 30 which is formed between the upper and lower valve plates. Alternatively, of course, instead of using the valve plate, by directly changing the gap between the valve seat having variable length and the relatively fixed portion for forming the gas flow gap, the temperature compensation may be implemented. The lower valve plate is sealed with respect to the valve seat by a first sealing member, and the upper valve plate is sealed with respect to the main gas path block sealed by a second sealing member, which can prevent the dilution bypass gas flow from leaking. The sealing members may be O-shaped resilient sealing ring or other elements having sealing effect.

The valve seat 24, which may be implemented as a metal body of a temperature linear expansion coefficient, has opposite top portion 241 and bottom portion 242, as well as a middle portion 243 between the top and bottom portions. As the temperature of the liquid anesthetic agent rises or drops, the length of the valve seat is lengthened (the spacing between the top and bottom portions increases) or shortened (the spacing between the top and bottom portions decreases). The top portion 241 of the valve seat 24 may be fixed while the bottom portion 242 of the valve seat is hermetically fitted with the bottom wall 101 of the vaporizing chamber 10 (i.e., the top portion 241 is restricted while the bottom portion 242 is free). Of course, alternatively the middle portion 243 of the valve seat 24 is fixed (i.e., both the top and bottom portions are free), or, the bottom portion 242 is fixed (i.e., the bottom portion 242 is restricted while the top portion 241 is free). The valve seat 24 may be made of a non-copper metal with relatively high temperature linear expansion coefficient, of which the cost is lower than copper and which is lightweight so that the weight of the whole anesthetic vaporizer is reduced to facilitate carrying and transportation. Of course, the valve seat may alternatively use copper or other metals, may alternatively use monometals or alloys, or otherwise other materials if they do not react with the liquid anesthetic agent and have good property of expanding when heated and contracting when cooled.

The anesthetic vaporizer may include an fresh gas inlet, a mixed gas outlet, a main gas path block having a gas flow passage and a vaporizing chamber having a bottom wall. The fresh gas inlet is connected with the gas flow passage via a branch circuit through which a dilution bypass gas flow passes and a branch circuit through which a carrier gas flow passes. The gas flow passage is communicated with the mixed gas outlet. The branch circuit through which the dilution bypass gas flow passes may include a bypass circuit and a temperature compensation unit arranged in sequence. The branch circuit through which the carrier gas flow passes may include a wick unit which is provided within the vaporizing chamber. The temperature compensation unit has a gas flow gap formed between the upper and lower valve plates. For the branch circuit through which the dilution bypass gas flow passes, the dilution bypass gas flow sequentially flows through the bypass circuit, the gas flow gap and the fluid passage; for the branch circuit through which the carrier gas flow passes, the carrier gas flow flows through the wick unit and carries the anesthetic vapor then flows into the fluid passage. For the branch circuit through which the carrier gas flow passes, it may additionally be provided with a pressure compensation unit and a fresh gas cut-off valve. The pressure compensation unit, the fresh gas cut-off valve and the wick unit are connected with one another in sequence. The anesthetic vaporizer may additionally include a concentration control unit provided in the fluid passage. The branch circuit through which the dilution bypass gas flow passes and the branch circuit through which the carrier gas flow passes concentrate at the side of the concentration control unit that is used for gas input. The side of the concentration control unit that is used for gas output is communicated with the mixed gas outlet. Since the bottom portion of the valve seat is hermetically fitted with the bottom wall of the vaporizing chamber, the valve seat will directly contact with the liquid anesthetic agent regardless of the level of the liquid agent, as long as there is the liquid anesthetic agent in the vaporizing chamber; therefore, the efficiency of heat exchange is high and the effect of temperature compensation is good.

The above describes the invention in detail in conjunction with specific preferred embodiments, but the invention should not be considered to be limited to the embodiments. It will be apparent to those skilled in the art that various modifications and changes may be made without departing from the essence of the invention and should be considered to fail into the scope of the invention.

What is claimed is:

1. A temperature compensation unit for an anesthetic vaporizer, which cooperates with a vaporizing chamber having a bottom wall, comprising:
   a first device comprising a first valve seat that has a bottom portion, which is hermetically connected to the bottom wall of the vaporizing chamber, such that at least a part of the bottom portion of the first valve seat contacts a liquid anesthetic agent in the vaporizing chamber, wherein
      at least the bottom portion of the first valve seat changes in length according to temperature changes in the liquid anesthetic agent that is in direct contact with at least the part of the bottom portion of the first valve seat to change a flow rate by moving at least the first valve seat to compensate for the temperature changes in the liquid anesthetic agent;
   a second device connected to the vaporizing chamber; and
   a gas flow gap through which a gas flow passes, wherein
      the gas flow gap is formed between the first device and the second device, and
      the gas flow gap becomes larger as temperature of the liquid anesthetic agent rises and smaller as the temperature of the liquid anesthetic agent drops.

2. The temperature compensation unit for an anesthetic vaporizer according to claim 1, in which the first device comprises:
   a lower valve plate connected to the first valve seat, the first valve seat being situated within the vaporizing chamber, the second device comprises an upper valve plate, the lower valve plate being positioned below the upper valve plate, the gas flow gap being formed between the upper valve plate and the lower valve plate,
      when the temperature of the liquid anesthetic agent rises, the first valve seat is lengthened with the lower valve plate moving downwards relative to the upper valve plate, and
      when the temperature of the liquid anesthetic agent drops, the first valve seat is shortened with the lower valve plate moving upwards relative to the upper valve plate.

3. The temperature compensation unit for the anesthetic vaporizer according to claim 2, in which the temperature compensation unit further comprises a valve rod, the lower valve plate being fixed on a top of the valve rod, a bottom of the valve rod being connected to the bottom portion of the first valve seat, wherein the thermal expansion coefficient of the first valve seat is greater than that of the valve rod.

4. The temperature compensation unit for the anesthetic vaporizer according to claim 3, in which the temperature compensation unit further comprises a screw adjuster, the bottom of the valve rod passing downwards through the bottom portion of the first valve seat and being attached to the screw adjuster.

5. The temperature compensation unit for anesthetic vaporizer according to claim 4, in which a diameter of the lower valve plate is greater than that of the valve rod, the first valve seat comprising an installation groove extending from a top portion thereof to the bottom portion thereof, wherein the installation groove comprises a first installation groove of a larger inner diameter and a second installation groove of a smaller inner diameter, the lower valve plate being situated in the first installation groove and sealed with respect to the first valve seat with a first sealing member, and the valve rod extending into the second installation groove.

6. The temperature compensation unit for anesthetic vaporizer according to claim 4, in which the upper valve plate is fixedly attached to a main gas path block.

7. The temperature compensation unit for anesthetic vaporizer according to claim 6, in which the upper valve plate has a through hole, wherein the gas flow gap, the through hole, and a gas flow passage are communicated with one another.

8. The temperature compensation unit for the anesthetic vaporizer according to claim 7, in which the upper valve plate is sealed with respect to a main gas path block by a second sealing member.

9. The temperature compensation unit for the anesthetic vaporizer according to claim 4, in which top portion of the first valve seat is fixed.

10. An anesthetic vaporizer, comprising:
    an fresh gas inlet and a main gas path block having a gas flow passage, the fresh gas inlet communicating with the gas flow passage via a first gas branch circuit and a second gas branch circuit, the gas flow passage communicating with a mixed gas outlet, the first gas branch circuit comprising:
    a bypass circuit and a temperature compensation unit arranged in sequence; and
    the second gas branch circuit comprising a wick unit which is provided within a vaporizing chamber, in which the temperature compensation unit comprises:
       a first device comprising a first valve seat that has a bottom portion, which is hermetically connected to a bottom wall of the vaporizing chamber, such that at least a part of the bottom portion of the first valve seat directly contacts a liquid anesthetic agent in the vaporizing chamber, wherein
          at least the bottom portion of the first valve seat changes in length according to temperature changes in the liquid anesthetic agent that is in direct contact with at least the part of the bottom portion of the first valve seat to change a flow rate by moving at least the first valve seat compensate for the temperature changes in the anesthetic agent;
       a second device connected with the vaporizing chamber via the main gas path block; and
       a gas flow gap with which the gas flow passage is communicated, wherein
          the gas flow gap is formed between the first device and the second device, and
          the gas flow gap becomes larger as temperature of the liquid anesthetic agent rises and smaller as the temperature of the liquid anesthetic agent drops.

11. The anesthetic vaporizer according to claim 10, in which the first device comprises:
  a lower valve plate connected with the first valve seat, wherein
    the first valve seat is situated within the vaporizing chamber, in which
    the second device comprises an upper valve plate, the lower valve plate being positioned below the upper valve plate, the gas flow gap being formed between the upper valve plate and the lower valve plate,
  when temperature of the liquid anesthetic agent rises, the first valve seat is lengthened with the lower valve plate moving downwards relative to the upper valve plate; and
  when the temperature of the liquid anesthetic agent drops, the first valve seat is shortened with the lower valve plate moving upwards relative to the upper valve plate.

12. The anesthetic vaporizer according to claim 11, in which the temperature compensation unit further comprises a valve rod and a screw adjuster, the lower valve plate being fixedly attached to a top of the valve rod, a bottom of the valve rod passing downwards through the bottom portion of the first valve seat and being attached to the screw adjuster, wherein a thermal expansion coefficient of the first valve seat is greater than that of the valve rod.

13. The anesthetic vaporizer according to claim 12, in which the upper valve plate is fixed with respect to the main gas path block and has a through hole, wherein the bypass circuit, the gas flow gap, the through hole, and the gas flow passage are communicated with one another.

14. The anesthetic vaporizer according to claim 13, in which a top portion of the first valve seat is fixed.

15. The anesthetic vaporizer according to claim 12, in which the gas flow passage is provided with a concentration control unit, wherein the first gas branch circuit and the second gas branch circuit are communicatively coupled to the concentration control unit, and the concentration control unit is communicated with a mixed gas outlet.

16. The anesthetic vaporizer according to claim 15, in which the second gas branch circuit further comprises a pressure compensation unit and a fresh gas cut-off valve, wherein the pressure compensation unit, the fresh gas cut-off valve, and a wick unit are communicatively coupled.

17. A temperature compensation unit for an anesthetic vaporizer, comprising:
  a lower valve assembly comprising a lower valve seat that extends to a bottom wall of a vaporizing chamber and has a bottom portion that changes in length according to temperature changes in a liquid anesthetic agent in a vaporizing chamber to compensate for the temperature changes and is attached to the bottom wall of the vaporizing chamber; and
  an upper valve assembly which is to cooperate with the lower valve assembly to adjust a concentration of a mixed anesthetic flow based at least in part upon the temperature changes, wherein
    a gas flow gap is formed by the upper valve assembly and the lower valve assembly, and
    a change in the length of the lower valve assembly causes a corresponding change in a dimension of the gas flow gap.

18. The temperature compensation unit of claim 17, further comprising an adjuster to adjust or calibrate a first size of the gas flow gap.

19. The temperature compensation unit of claim 17, wherein the lower valve seat is fixed on a top portion of the lower valve seat so the top portion remains stationary in presence of the temperature changes in the liquid anesthetic agent, and the lower valve seat that is attached to the bottom wall of the vaporizing chamber has at least one degree of freedom near the bottom wall of the vaporizing chamber to accommodate the temperature changes.

20. The temperature compensation unit of claim 17, wherein the lower valve seat is fixed on a middle portion of the lower valve seat so the middle portion remains stationary in presence of the temperature changes in the liquid anesthetic agent, and the lower valve seat that is attached to the bottom wall of the vaporizing chamber has at least one degree of freedom near the bottom wall of the vaporizing chamber to accommodate the temperature changes.

* * * * *